United States Patent [19]

Toda et al.

[11] Patent Number: 5,229,371
[45] Date of Patent: Jul. 20, 1993

[54] CHEMICAL MODIFICATION OF ELSAMICIN A AT THE 3' AND/OR 4' OH GROUPS

[75] Inventors: Soichiro Toda, Tokyo; Haruhiro Yamashita, Chiba; Takayuki Naito, Kawasaki; Yuji Nishiyama, Tokyo, all of Japan

[73] Assignee: Bristol-Myers Squibb Company, New York, N.Y.

[21] Appl. No.: 974,376

[22] Filed: Nov. 10, 1992

Related U.S. Application Data

[63] Continuation of Ser. No. 707,471, May 30, 1991, abandoned.

[51] Int. Cl.$^5$ .................. A61K 31/71; C07H 17/04
[52] U.S. Cl. .................. 514/27; 514/34; 536/16.8; 536/17.5; 536/17.2; 536/18.1
[58] Field of Search .................. 514/27, 34; 536/17.5, 536/17.2, 18.1, 16.8

[56] References Cited

U.S. PATENT DOCUMENTS

| | | | |
|---|---|---|---|
| 4,518,589 | 5/1985 | Konishi et al. | 536/18.1 |
| 4,760,136 | 7/1988 | Mori et al. | 536/18.1 |
| 4,927,919 | 5/1990 | Yamada et al. | 536/17.4 |
| 5,064,945 | 11/1991 | Yamada et al. | 536/17.5 |
| 5,149,793 | 9/1992 | Yamada et al. | 536/16.8 |

OTHER PUBLICATIONS

McOmie, J. F. W., *Protective Groups in Organic Chemistry*, pp. 117–118, 1973.
Konishi, et al., *J. Antibiotics*, 39: 784–791, (1986).
Sugawara, et al., *J. Org. Chem.*, 52: 996–10001, (1987).
Leach, et al., *J. Am. Chem. Soc.*, 75: 4011–4012, (1953).
*In progress in Medicinal Chemistry*, Ed., G. P. Ellis & G. B. West 19; pp. 247–268, Elsevier Biomedical Press Amsterdam, (1982).
Simonitsch, et al., Uber die Struktur des Chartreusins I, *Helv. Chim. Acta*, 47: 1459–1475, (1964).
Eisenhuth, et al, Uber die Struktur des Chartreusins II, *Helv. Chim. Acta*, 47, 1475–1484, (1964).

*Primary Examiner*—Johnnie R. Brown
*Assistant Examiner*—A. Varma
*Attorney, Agent, or Firm*—Michelle A. Kaye

[57] ABSTRACT

This invention relates to novel elsamicin A derivatives having an alkylidene group on the 3' and 4'-OH group or a tetrahydropyranyl group on the 4'-OH group, a process for producing said elsamicin A derivatives, antitumor composition containing the same as the active ingredient, and a method for therapy using said compositions.

4 Claims, No Drawings

CHEMICAL MODIFICATION OF ELSAMICIN A AT THE 3' AND/OR 4' OH GROUPS

This application is a continuation of application Ser. No. 07/707,471, filed May 30, 1991, abandoned.

BACKGROUND OF THE INVENTION

1. Field of the Invention

This invention relates to novel elsamicin A derivatives which have improved antitumor activity, to their production, to compositions containing the same as the active ingredient, and a method for therapy using said compositions.

2. Description of the Prior Art

Elsamicin A is an antitumor antibiotic produced by cultivating an elsamicin A-producing strain of actinomycete designated strain J907-21 (ATCC 39417), or a mutant thereof. Elsamicin A exhibits antibacterial activity against aerobic gram-positive bacteria and anaerobic bacteria. It also exerts activity against various murine tumor cells including leukemia P388, lymphoid leukemia L1210, and melanotic melanoma B16 in vitro and in vivo. Konishi, et al, Elsamicins, new antitumor antibiotics related to chartreusin. I. Production, isolation, characterization and antitumor activity, *J. Antibiotics*, 39: 784–791, (1986); U.S. Pat. No. 4,518,589 to Konishi, et al, issued May 21, 1985.

The structure of elsamicin A (Formula I, below) has been determined and shown to be closely related to chartreusin (Formula II, below). Sugawara, et al, Elsamicins A and B, new antitumor antibiotics related to chartreusin. II. Structures of elsamicins A and B. *J. Org. Chem.*, 52: 996–1001, (1987).

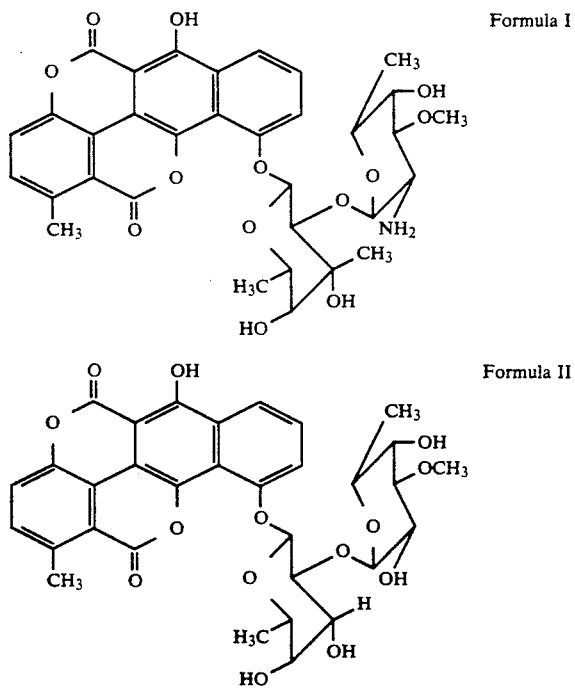

Both elsamicin A and chartreusin have the same aglycone, chartarin, but the antibiotics differ in the disaccharide moiety. Leach, et al, Chartreusin, a new antibiotic produced by *Streptomyces chartreusis*, a new species, *J. Am. Chem. Soc.*, 75: 4011–4012, (1953); Beisler, J. A., Chartreusin, a glycosidic antitumor antibiotic for Streptomyces, *In progress in Medicinal Chemistry*, Ed., G. P. Ellis and G. B. West 19: pp. 247–268, Elsevier Biomedical Press Amsterdam, (1982); Simonitsch, et al: Über die Struktur des Chartreusins I, *Helv. Chim. Acta*, 47: 1459–1475, (1964); Eisenhuth, et al, Über die Struktur des Chartreusins II, *Helv. Chim. Acta*, 47, 1475–1484, (1964). Interconversion of both compounds by chemical process has never been reported.

In the course of chemical modification of elsamicin A, we found that introduction of alkylidene group on the 3' and 4'-OH groups, or a tetrahydropyranyl group on the 4'-OH group led to an increase of antitumor activity of elsamicin A.

SUMMARY OF THE INVENTION

The present invention provides new derivatives of elsamicin A which exhibit improved antitumor activity. More particularly the present invention describes the chemical modification on the 3' and/or 4'-OH groups of elsamicin A.

This invention further provides an antitumor composition comprising, as the active ingredient, at least one member selected from the group consisting of the elsamicin A derivative of the present invention.

This invention further provides a method for therapy of cancer using the above antitumor composition.

Further provided is a process for producing the above-mentioned elsamicin A derivative.

DETAILED DESCRIPTION

U.S. Pat. No. 4,518,589 to Konishi et al, discloses the production and isolation of the antitumor agent designated elsamicin A. (Formula I, above). The above-mentioned elsamicin A compound is the principal component of the fermentation of the elsamicin A-producing strain of actinomycete, designated strain J907-21 (ATCC 39417).

It has now been found according to the present invention that chemical modification on the 3' and/or 4'-OH groups of elsamicin A leads to new derivatives having improved antitumor activity.

The elsamicin A derivatives of the present invention have the general Formula III and IV below

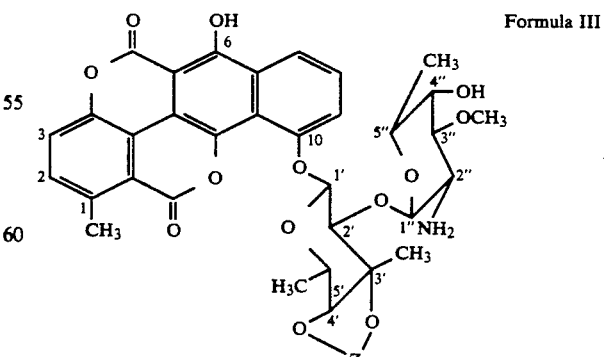

wherein Z is alkylidene, cycloalkylidene, arylalkylidene or alkoxyalkylidene.

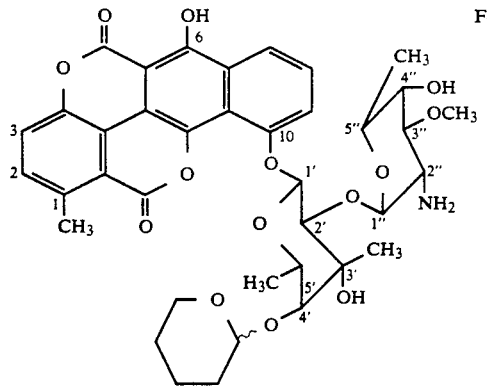

Formula IV

As shown in Scheme 1, the 3',4'-O-alkylidenation of elsamicin A (1) was carried out, by treatment of 2"-N-protected elsamicin A (3 or 4) with dimethyl acetals of an appropriate ketone or aldehyde in the presence of acid catalysts to give intermediates, 5 and 7, followed by subsequent deprotection which afforded the 3',4'-O-alkylidene derivatives (6a–6d). Isopropylidene (6a) and benzylidene (6c) were also prepared from elsamicin A without N-protection. As shown in Scheme 2, reaction of compound 1 with dihydropyran in the present of an acid catalyst gave a mixture of per-tetrahydropyranyl (THP) derivatives, which was treated with p-toluenesulfonic acid (TsOH) in methanol to afford the mono-O-THP derivative (8).

Based on the mass spectrum, the structure of 8 was determined to be the 4'-O-THP derivative.

Table 1 indicates the compounds of the present application and their respective number.

TABLE 1

Compounds of the present invention and their respective number

| Compound No. | Name |
|---|---|
| 1 | Elsamicin A |
| 2 | Chartreusin |
| 3 | 2"-N-t-Butoxycarbonylelsamicin A |
| 4 | 2"-N-Benzyloxycarbonylelsamicin A |
| 5a | 2"-N-t-Butoxycarbonyl-3',4'-O-isopropylideneelsamicin A |
| 5b | 2"-N-t-Butoxycarbonyl-3',4'-O-cyclohexylideneelsamicin A |
| 5c | 3'4'-O-Benzylidene-2"-N-t-butoxycarbonylelsamicin A |
| 6a | 3',4'-O-Isopropylideneelsamicin A |
| 6b | 3',4'-O-Cyclohexylideneelsamicin A |
| 6c | 3',4'-O-Benzylideneelsamicin A |
| 6d | 3',4'-O-Methoxymethylideneelsamicin A |
| 7a | 2"-N-Benzyloxycarbonyl-3',4'-O-isopropylideneelsamicin A |
| 7d | 2"-N-Benzyloxycarbonyl-3',4'-O-methoxymethylideneelsamicin A |
| 8 | 4'-O-Tetrahydropyranylelsamicin A |

Scheme 1
Synthetic Route of 3', 4'-O-Alkylidene Derivatives of Elsamicin A

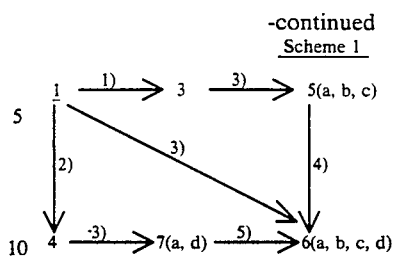

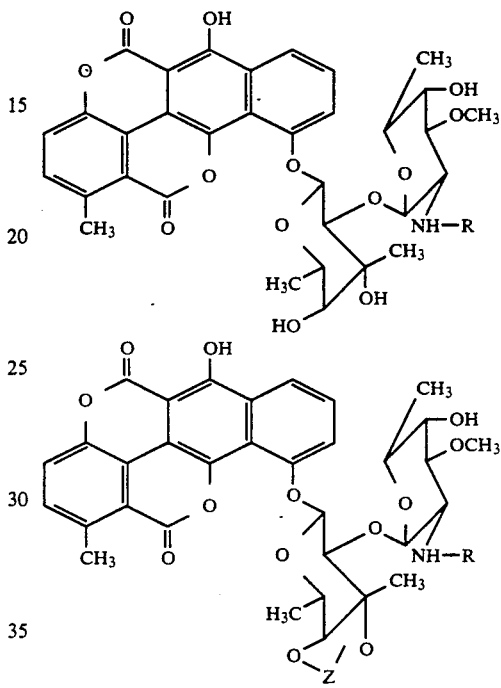

3 R = t-BOC
4 R = R = Cbz
5 R = t-BOC
6 R = R = H
7 R = Cbz 1) (t-BOC)$_2$O/NEt$_3$

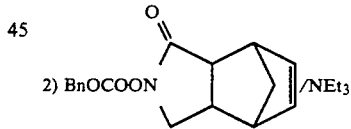

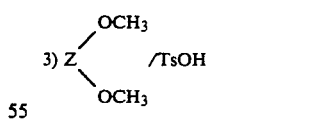

4) TsOH or TFA

5) H$_2$/Pd-C

Z: (a) 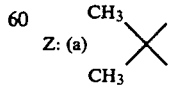

(b)

-continued
Scheme 1

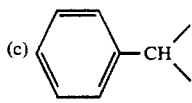

(c)

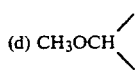

(d) CH₃OCH

Scheme 2
Preparation of 4'-O-Tetrahydropyranylelsamicin A

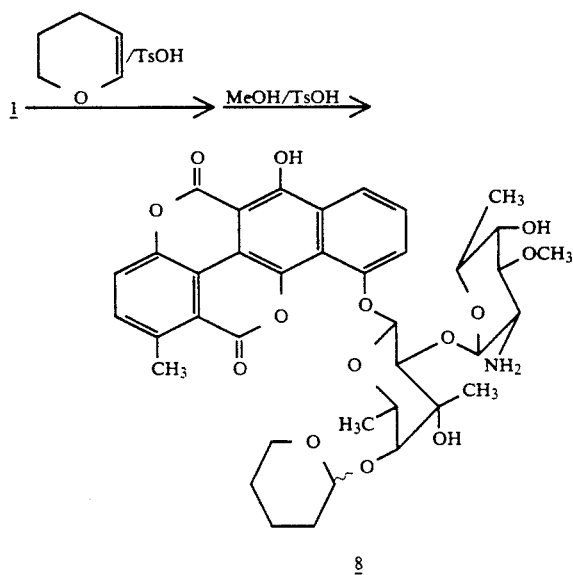

8

Antitumor activity of 3'- and/or 4'-O-modified elsamicin A derivatives

Five 3'- and/or 4'-O-modified elsamicin A derivatives were synthesized and comparatively tested with the parent compound for in vitro and in vivo antitumor activities.

For in vitro cytotoxicity experiment, murine melanoma B16-F10 cells were grown and maintained in Eagle's minimum essential medium (Nissui), which contains kanamycin (60 μg/ml), supplemented with heat-inactivated fetal calf serum (10%) and non-essential amino acids (0.6%) at 37° C. under a humidified atmosphere in a 5% $CO_2$ incubator. Exponentially growing B16-F10 cells were harvested, counted and suspended in the culture medium at the concentration of $2.0 \times 10^4$ cells/ml. The cell suspension (180 μl) was planted into wells of a 96-well microtiter plate and incubated for 24 hours. Test compound (20 μl) were added to the wells and the plates were further incubated for 72 hours. The cytotoxic activity was colorimetrically determined at 540 nm after staining viable cells with neutral red solution. All of the 3'-and/or 4'-O-modified elsamicin A derivatives tested showed quite strong cytotoxicity against B16-F10 cells with the $IC_{50}$ values of 0.025-0.07 μg/ml (Table 2).

In vivo antitumor activity of the above five derivatives was tested in the lymphocytic leukemia P388 and melanoma B16 systems. Female $CDF_1$ (for P388) and male $BDF_1$ (for B16) mice were inoculated by ip injection at $10^6$ P388 cells and 0.5 ml of a 10% B16 brei per mouse, respectively (day 0). Test compounds were introperitoneally administered to the mice once daily on days 1 to 3 (Q1Dx3) in the P388 system or once a day on days 1, 5 and 9 (Q4Dx3) in the B16 system and animals were observed for 50 days.

The percent increase of median survival time (MST) of treated animals over that of untreated control animals was determined and reported as T/C %. Compounds showing T/C % values of 125 or greater are considered to have significant antitumor activity. As shown in Table 2, among the above five derivatives, 4'-O-tetrahydropyranylelsamicin A, (8) was the most interesting compound in the P388 system. It showed three times more potent minimum effective dose (MED) than elsamicin A and high T/C % values. 3',4'-O-Isopropylideneelsamicin A, (6a), 3',4'-O-benzylideneelsamicin A, (6c) and 3',4'-O-methoxymethylideneelsamicin A, (6d) were as active as the parent compounds in terms of MED. In the B16 system, all of five derivatives tested showed good response to the tumor (Table 3). Similar to the results in the P388 system, compound 8 was better than elsamicin A (1) in terms of MED and T/C % values. Some survivors were observed on day 50 in the groups tested with 3~20 mg/kg/day of this compound. Compound 6d also gave extremely potent therapeutic activity with higher T/C % values at 3 and 10 mg/kg/day than elsamicin A (1).

TABLE 2

In vitro cytotoxicity against B16-F10 melanoma and in vivo antitumor activity against P388 leukemia in mice.

| Compound | Z | Cytoxicity $IC_{50}$ (μg/ml) | T/C % of MST[*1] |||||| 
|---|---|---|---|---|---|---|---|---|
|  |  |  | 20[*2] | 10 | 3 | 1 | 0.3 | 0.1 |
| 6a | ⨯CH₃ / CH₃ | 0.025 |  |  | 210 | 170 | 140 | 120 |
| 6b | (cyclohexyl) | 0.04 |  | 165 | 175 | 140 | 120 |  |
| 6c | ⨯C₆H₅ / H | 0.07 | Tox | 180 | 165 | 150 | 130 | 110 |
| 6d | ⨯OCH₃ / H | 0.05 | Tox | 224 | 167 | 167 | 137 | 124 |

TABLE 2-continued

In vitro cytotoxicity against B16-F10 melanoma and in vivo antitumor activity against P388 leukemia in mice.

| Compound | Z | Cytoxicity $IC_{50}$ (μg/ml) | T/C % of MST[*1] | | | | | |
|---|---|---|---|---|---|---|---|---|
| | | | 20[*2] | 10 | 3 | 1 | 0.3 | 0.1 |
| 8 | | 0.04 | Tox | 225 | 190 | 168 | 145 | 130 |
| Elsamicin A (1) | | 0.03 | Tox | 190 | 180 | 155 | 140 | 123 |

[*1]Median survival time in days
[*2]Dose in mg/kg/day, Q1D × 3, ip

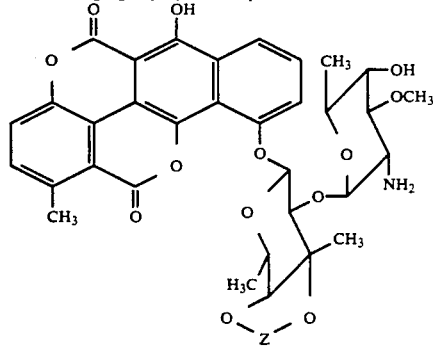

6

TABLE 3

In vivo antitumor activity against B16 melanoma in mice

| Compound | T/C % of MST[*1] | | | | | |
|---|---|---|---|---|---|---|
| | 20[*2] | 10 | 3 | 1 | 0.3 | 0.1 |
| 6a | | 82 | 192 | 166 | 116 | 105 |
| 6b | | 200 | 175 | 132 | 111 | |
| 6c | | 186 | 179 | 136 | 114 | 121 |
| 6d | | ≧333 (⅓)[*3] | 283 | 167 | 137 | 120 |
| 8 | ≧370 (⅓) | ≧330 (2/4) | ≧281 (⅓) | 248 | 159 | 133 |
| 1 | | ≧298 (2/12) | ≧216 (2/12) | 179 | 139 | 116 |

[*1]Median survival time in days
[*2]Dose in mg/kg/day, Q4D × 3 ip
[*3]No. of survivors/tested on day 50

The present invention includes within its scope a process for producing the elsamicin A derivatives of the present invention.

Another aspect of the invention, there are provided pharmaceutical compositions which comprise an effective tumor-inhibiting amount of the compound of Formula III or IV, in combination with an inert pharmaceutically acceptable carrier or diluent.

According to another aspect of the invention provides a method for therapeutically treating an animal, preferably mammalian, host affected by a tumor which comprises administering to such host an effective tumor-inhibiting dose of the antibiotic of the compound of Formula III or IV.

Examples of suitable compositions include solid compositions for oral administration such as tablets, capsules, pills, powders and granules, liquid compositions for oral administration such as solutions, suspensions, syrups and elixirs and preparations for parenteral administration such as sterile solutions, suspensions or emulsions. They may also be manufactured in the form of sterile solid compositions which can be dissolved in sterile water, physiological saline or some other sterile injectable medium immediately before use.

It will be appreciated that the actual preferred dosages of the elsamicin A derivative of the present invention will vary according to the particular compound being used, the particular composition formulated, the mode of application and the particular situs, host and disease being treated. Many factors that modify the action of the drug will be taken into account by those skilled in the art, e.g. age, body weight, sex, diet, time of administration, rate of excretion, condition of the host, drug combinations, reaction sensitivities and severity of the disease. Administration can be carried out continuously or periodically within the maximum tolerated dose. Optimal application rates for a given set of conditions can be readily ascertained by those skilled in the art using conventional dosage determination tests.

The present invention is illustrated by the following examples which are not intended to be construed as limiting the scope of the invention.

Specific synthesis examples of the intermediates 3-5c, 7a and 7d are explained below, from which intermediates the compounds of this invention 6a-6d and 8 are synthesized by the above process.

EXAMPLE 1

Synthesis of 2''-N-t-Butoxycarbonylelsamicin A (3)

A mixture of elsamicin A (653 mg, 1 mmole), di-t-butyl dicarbonate (348 mg, 1.6 mmoles) and triethylamine (0.14 ml, 1 mmole) in dioxane (10 ml) was stirred at room temperature overnight. The reaction mixture was evaporated in vacuo to give a semi-crystalline residue, which was recrystallized from $CH_2Cl_2$/ether to obtain 768 mg (100%) of compound 3 as yellowish crystalline powder.

MP 183°-184° C. IR $\nu_{max}$ (KBr) cm$^{-1}$ 3410, 1700, 1505, 1370, 1255, 1120, 1065, 875, 780. UV $\lambda_{max}$ (MeOH)nm (ε) 236 (38300), 266 (37800), 333 (6180), 380 (8770), 400 (14500), 423 (15900). $^1$H NMR (CDCl$_3$) δ 0.73 (9H, br.s.), 1.31 (3H, d, J=7.0 Hz), 1.36 (3H, s), 1.39 (3H, d, J=6 Hz), 2.68 (3H, s), 3.35 (3H, s), 5.37 (1H, d, J=8.0 Hz), 4.66 (1H, d, J=4 Hz), 8.18 (1H, dd, J=8.0 & 1.5 Hz), 11.59 (1H, s).

Anal. Calcd. for $C_{38}H_{43}NO_{15}.H_2O$: C 59.14, H 5.88, N 1.81. Found: C 59.12, H 6.06, N 2.27.

EXAMPLE 2

Synthesis of 2''-N-Benzyloxycarbonylelsamicin A (4)

To a stirred suspension of elsamicin A (653 mg), $NEt_3$ (0.14 ml) in dioxane (10 ml) was added N-benzyloxycarbonyloxy-5-norbornene-2,3-dicarboximide (334 mg). The reaction mixture was stirred overnight at room temperature and evaporated in vacuo. The residue was dissolved in $CH_2Cl_2$ and the solution was washed with diluted aqueous $NaHCO_3$, water and saturated aqueous NaCl, successively, dried with $MgSO_4$ and concentrated under reduced pressure to give a yellow mass. The residue was chromatographed on a silica gel column (Wakogel C-200, 21×80 mm) using 2% $MeOH/CHCl_3$ as an eluant to give 772 mg (98%) of the title compound.

MP 166°–167° C. IR $\nu_{max}$ (KBr) cm$^{-1}$ 1730, 1695, 1510, 1380, 1260, 1240, 1150, 1070, 785. UV $\lambda_{max}$ (MeOH)nm ($\epsilon$) 236 (38900), 266 (38500), 335 (6480), 381 (9190), 401 (15300), 423 (16600). $^1$H NMR (CDCl$_3$) $\delta$ 1.32 (3H, d, J=6 Hz), 1.38 (3H, s), 2.74 (3H, s), 3.36 (3H, s), 5.39 (1H, d, J=8 Hz), 5.74 (1H, d, J=4 Hz), 8.08 (1H, dd, J=8 & 1.5 Hz), 11.41 (1H, s).

Anal. Calcd. for $C_{41}H_{41}NO_{15}\cdot\frac{1}{2}H_2O$: C 61.80, H 5.31, N 1.76. Found: C 61.92, H 5.14, N 2.23.

EXAMPLE 3

Synthesis of 2''-N-t-Butoxycarbonyl-3',4'-O-isopropylideneelsamicin A (5a)

To a solution of compound 3 (200 mg) and 2,2-dimethoxypropane (1.2 ml) in dry $CH_2Cl_2$ (4 ml) was added TsOH (5 mg) and the mixture was kept at room temperature overnight. Saturated aqueous $NaHCO_3$ was added to the reaction mixture and the organic layer was taken up, dried with $MgSO_4$ and evaporated in vacuo to give 190 mg (90%) of the title compound as a yellow solid.

MP 168°–169° C. IR $\nu_{max}$ (KBr) cm$^{-1}$ 3420, 1740, 1690, 1505, 1375, 1250, 1065, 780. UV $\lambda_{max}$ (MeOH)nm ($\epsilon$) 236 (40600), 266 (39100), 333 (6370), 380 (8850), 399 (14200), 422 (15500). $^1$H NMR (CDCl$_3$) $\delta$ 1.34 (3H, d, J=6 Hz), 1.37 (3H, d, J=7 Hz), 1.37 (3H, s), 1.42 (3H, s), 1.68 (3H, s), 3.35 (3H, s), 5.23 (1H, d, J=8 Hz), 5.8 (1H, d, J=4 Hz), 8.33 (1H, dd, J=8 & 1.5 Hz), 11.63 (1H, br.).

Anal. Calcd. for $C_{41}H_{47}NO_{15}\cdot H_2O$: C 60.66, H 6.08, N 1.73. Found: C 60.92, H 6.03, N 2.00.

EXAMPLE 4

Synthesis of 2''-N-Benzyloxycarbonyl-3',4'-O-isopropylideneelsamicin A (7a)

To a solution of compound 4 (507 mg) and 2,2-dimethoxypropane (2.9 ml) in dry dichloromethane (10 ml) was added p-toluenesulfonic acid (10 mg) and the mixture was kept at room temperature overnight. Saturated aqueous $NaHCO_3$ (10 ml) was added to the reaction mixture and the organic layer was separated, dried over $MgSO_4$ and evaporated under reduced pressure. The residue was triturated with a mixture of $CH_2Cl_2$-ether-n-hexane to give 540 mg (100%) the title compound.

MP 160°–162° C. IR $\nu_{max}$ (KBr) cm$^{-1}$ 1730, 1690, 1500, 1375, 1250, 1140, 1065, 780. UV $\lambda_{max}$ (MeOH)nm ($\epsilon$) 236 (39100), 267 (37600), 333 (6440), 380 (9020), 400 (14400), 422 (15500). $^1$H NMR (CDCl$_3$) $\delta$ 1.28 (3H, d, J=6 Hz), 1.40 (3H, d, J=7 Hz), 1.41 (3H, s), 1.47 (3H, s), 1.70 (3H, s), 2.88 (3H, s), 3.45 (3H, s), 5.28 (1H, d, J=8 Hz), 5.66 (1H, d, J=4 Hz), 8.32 (1H, dd, J=8 & 2 Hz), 11.53 (1H, br.).

Anal. Calcd. for $C_{44}H_{45}NO_{15}$: C 63.84, H 5.48, N 1.69. Found: C 63.59, H 5.64, N 1.63.

EXAMPLE 5

Synthesis of 3',4'-O-Isopropylideneelsamicin A (6a)

Method A

A solution of compound 7a (67 mg) in 80% aqueous tetrahydrofuran (2.5 ml), was hydrogenated in the presence of 10% Pd-C (30 mg) for 1.5 hour. The reaction mixture was filtered to remove the catalyst and then concentrated to dryness. The residue was purified by column chromatography using 5% MeOH in CHCl$_3$ as an eluant to give 47 mg (83%) of the title compound.

MP 189°–191° C. (dec.). IR $\nu_{max}$ (KBr) cm$^{-1}$ 1710, 1610, 1370, 1250, 1070, 780. UV $\lambda_{max}$ (MeOH)nm ($\epsilon$) 236 (34500), 266 (29700), 332 (4980), 399 (10600), 420 (11300). $^1$H NMR (CDCl$_3$+CD$_3$OD) $\delta$ 1.18 (3H, d, J=6 Hz), 1.29 (3H, d, J=7 Hz), 1.39 (3H, s), 1.46 (3H, s), 1.67 (3H, s), 2.87 (3H, s), 3.52 (3H, s), 5.22 (1H, d, J=8 Hz), 6.02 (1H, br.).

Anal. Calcd. for $C_{36}H_{39}NO_{13}\cdot 3/2H_2O$: C 59.99, H 5.87, N 1.94. Found: C 60.09, H 5.76, N 2.13.

MS (SIMS) M/Z 695 (M+H)$^+$, 360, 334, 160.

Method B

A solution of compound 5a (238 mg) and p-toluenesulfonic acid monohydrate (TsOH) (285 mg) in acetone (5 ml) was stirred at room temperature for 2 hours and then concentrated in vacuo. The residue was dissolved in a mixture of methanol and chloroform (1:10, 40 ml). The solution was successively washed with 10% aqueous $NaHCO_3$, water and brine, and dried over $MgSO_4$ and concentrated in vacuo. The residue was purified by column chromatography on silica gel to give 142 mg (68%) of the title compound. MP 189°–191° C. The spectral and HPLC data of compound 6a obtained here was completely identical with those obtained in method A.

Method C

A mixture of compound 1 (262 mg), TsOH (80 mg) and 2,2-dimethoxypropane (1 ml) in dry $CH_2Cl_2$ (5 ml) was stirred at room temperature for 17 hours. A saturated aqueous $NaHCO_3$ was added to the reaction mixture and the organic layer was separated, dried over $Na_2SO_4$ and evaporated. The yellow residue was triturated with ether to afford 280 mg (100%) of 6a. MP 189°–191° C. The spectral and HPLC data of compound 6a obtained here was completely identical with those obtained in method A.

EXAMPLE 6

Synthesis of 2''-N-t-Butoxycarbonyl-3',4'-O-cyclohexylideneelsamicin A (5b)

A solution of compound 3 (151 mg), 1,1-dimethoxycyclohexane (1.2 ml) and anhydrous p-toluenesulfonic acid (3 mg) in dry $CH_2Cl_2$ (3 ml) was stirred at room temperature for 2 hours. The reaction mixture was diluted with $CH_2Cl_2$, washed with saturated aqueous $NaHCO_3$, dried over $MgSO_4$ and evaporated to give a crystalline residue, which was washed with ether to afford 165 mg (100%) of compound 5b.

MP 173°–175° C. IR $\nu_{max}$ (KBr) cm$^{-1}$ 2910, 1730, 1710, 1680 (sh), 1500. UV $\lambda_{max}$ (MeOH)nm ($\epsilon$) 236 (35300), 266 (34200), 333 (4660), 379 (7820), 399 (12500), 422 (13700). $^1$H NMR (CDCl$_3$) $\delta$ 0.69 (9H, s), 1.10–2.5 (19H, m), 2.90 (3H, s), 3.36 (3H, s), 5.22 (1H, d, J=8 Hz), 5.83 (1H, d, J=4 Hz), 11.69 (1H, s).

Anal. Calcd. for C$_{44}$H$_{51}$NO$_{15}$: C 63.38, H 6.16, N 1.68. Found: C 64.38, H 6.63, N 1.60.

EXAMPLE 7

Synthesis of 3′,4′-O-Cyclohexylideneelsamicin A (6b)

A solution of compound 5b (83.3 mg) and TsOH (95 mg) in cyclohexanone (1.6 ml) was stirred at room temperature overnight. An aqueous 10% NaHCO$_3$ (5 ml and CHCl$_3$ (10 ml) were added to the reaction mixture and the organic layer was taken up, washed with brine (5 ml), dried over MgSO$_4$ and evaporated in vacuo. The viscous residue was triturated with isopropyl ether to afford 32 mg (44%) of compound 6b.

MP 182°–190° C. (dec.). IR $\nu_{max}$ (KBr) cm$^{-1}$ 3400, 1605, 1445, 1370, 1230, 1170, 1070. UV $\lambda_{max}$ (MeOH)nm ($\epsilon$) 236 (33000), 266 (28900), 331 (5340), 399 (10100), 420 (10500), H NMR (CDCl$_3$+CD$_3$OD) $\delta$ 1.1–1.2 (19H, m), 2.87 (3H, s), 3.45 (3H, s), 5.23 (1H, d, J=8 Hz), 5.94 (1H, d, J=4 Hz).

Anal. Calcd. for C$_{39}$H$_{43}$NO$_{13}$.H$_2$O: C 62.31, H 6.03, N 1.86. Found: C 62.23, H 5 92, N 1.83.

EXAMPLE 8

Synthesis of 3′,4′-O-Benzylidene-2″-N-t-butoxycarbonylelsamicin A (5c)

To a solution of compound 3 (77 mg) and benzaldehyde dimethylacetal (0.5 ml) in CH$_2$Cl$_2$ (2 ml) was added TsOH (5 mg), and the mixture was kept at room temperature for 2 days. An aqueous saturated NaHCO$_3$ solution (ca. 10 ml) was added to the reaction mixture and the mixture was extracted with CHCl$_3$. The extract was washed with water, dried over Na$_2$SO$_4$ and evaporated in vacuo to give a yellow solid, which was purified by silica gel column chromatography using MeOH in CHCl$_3$ (1–3%) as eluants to afford 70 mg (81%) of the title compound.

MP 168°–170° C. IR $\nu_{max}$ (KBr) cm$^{-1}$ 1735 sh, 1695, 1505, 1375, 1255, 1235, 1145, 1070, 780. UV $\lambda_{max}$ (MeOH) nm ($\epsilon$) 235 (40600), 266 (39300), 332 (6410), 379 (8690), 399 (13900), 421 (15000). $^1$H NMR (CDCl$_3$) $\delta$ 0.71 (9H, s), 1.35 (3H, d, J=6 Hz), 1.58 (3H, s), 2.91 (3H, s), 3.40 (3H, s), 5.32 (1H, d, J=8 Hz), 5.69 (1H, d, J=4 Hz), 5.98 (1H, s).

Anal. Calcd. for C$_{45}$H$_{47}$NO$_{15}$.H$_2$O: C 62.86, H 5 74, N 1.63. Found: C 63.17, H 5.42, N 1.53.

EXAMPLE 9

Synthesis of 3′,4′-O-Benzylideneelsamicin A (6c)

Method A

Compound 5c (60 mg) was dissolved in TFA (0.3 ml), and the mixture was immediately concentrated in vacuo. The residue was dissolved in a mixture of saturated aqueous NaHCO$_3$ and CHCl$_3$. The organic layer was separated, washed with water and evaporated in vacuo. The yellow residue was chromatographed on a silica gel column to afford 24 mg (45%) of compound 6c.

MP 183°–189° C. IR $\nu_{max}$ (KBr) cm$^{-1}$ 1710, 1610, 1510, 1375, 1250, 1235, 1070, 780. UV $\lambda_{max}$ (MeOH)nm ($\epsilon$) 236 (40700), 266 (34400), 331 (5890), 379 (8180), 398 (12200), 420 (13000). 1H NMR (CDCl$_3$+CD$_3$OD) $\delta$ 0.82 (1.5H, d, J=6 Hz), 1.22 (3H, d, J=6 Hz), 1.36 (1.5H, d, J=6 Hz), 1.58 (1.5H, s), 1.61 (1.5H, s), 2.92 (3H, s), 3.53 (3H, s), 5.29 (1H, d, J=8 Hz), 5.95 (0.5H, s), 6.01 (0.5H, br.), 6. (0.5H, br.), 6.28 (0.5H, s).

MS (SIMS) M/Z 742 (M+H)$^+$, 408, 334, 160.

Method B

A mixture of elsamicin A (66 mg), benzaldehyde dimethylacetal (185 mg) and TsOH (25 mg) in CH$_2$Cl$_2$ (5 ml) was kept at room temperature for 2 hours. A saturated aqueous NaHCO$_3$ solution (ca. 10 ml) and CH$_2$Cl$_2$ (10 ml) were added to the reaction mixture. The organic layer was separated and evaporated under reduced pressure to give a yellow solid, which was purified by silica gel column chromatography using MeOH in CHCl$_3$ as an eluant to give 45 mg (60%) of 6c. The HPLC and spectral data of compound 6c obtained here was indistinguishable to those obtained in Method A.

EXAMPLE 10

Synthesis of 2″-N-Benzyloxycarbonyl-3′,4′-O-methoxymethylideneelsamicin A (7d)

A solution of compound 4 (62 mg), orthoformic acid trimethyl ester (0.2 ml) and p-toluenesulfonic acid (5 mg) in CH$_2$Cl$_2$ (3 ml) was stirred at room temperature for 2 hours, and the reaction mixture was diluted with CH$_2$Cl$_2$ (10 ml), washed with saturated aqueous NaHCO$_3$, dried over Na$_2$SO$_4$ and evaporated in vacuo to give 65 mg (100%) of compound 7d.

MP 139°–141° C. IR $\nu_{max}$ (KBr) cm$^{-1}$ 3400, 1725, 1510, 1375, 1255, 1240, 1070 UV $\lambda_{max}$ (MeOH)nm ($\epsilon$) 236 (35700), 267 (34000), 333 (5800), 380 (8090), 399 (13000), 422 (13900). 1H NMR (CDCl$_3$+D$_2$O) $\delta$ 1.32 (3H, d, J=6 Hz), 1.39 (3H, d, J=6.5 Hz), 1.56 (3H, s), 2.88 (3H, s), 3.92 (3H, s), 3.96 (3H, s), 6.25 (1H, d, J=8 Hz), 5.65 (1H, d, J=4 Hz), 5.93 (2H, s).

EXAMPLE 11

Synthesis of 3′,4′-O-Methoxymethylideneelsamicin A (6d)

A solution of compound 7d (57 mg) in 75% aqueous tetrahydrofuran (4 ml) was hydrogenated in the presence of 10% Pd-C (30 mg) for 1.5 hours at room temperature. The reaction mixture was filtered off and the filtrate was concentrated to dryness. The residue was purified by column chromatography on silica gel to give 35.5 mg (73%) of compound 6d.

MP 209°–211° C. (dec.). IR $\nu_{max}$ (KBr) cm$^{-1}$ 3400, 1720, 1680, 1375, 1255, 1205, 1120, 1075. UV $\lambda_{max}$ (MeOH)nm ($\epsilon$) 236 (33900), 266 (30800), 331 (5200), 398 (10800), 419 (11200). $^1$H NMR (CDCl$_3$+CD$_3$OD) $\delta$ 1.0–1.4 (6H, m), 1.57 (3H, s), 2.62 (3H, s), 3.38 (3H, s), 3.50 (3H, s), 5.44 (1H, d, J=8 Hz), 5.87 (2H, m).

MS (SIMS) M/Z 697 (M+2H)$^+$, 363, 334, 202, 160.

EXAMPLE 12

Synthesis of 4′-O-Tetrahydropyranylelsamicin A (8)

A solution of elsamicin A (110 mg) and dihydropyran (0.5 ml) in dimethylformamide (5 ml) was acidified by a small excess molar equivalents of TsOH and kept at room temperature overnight. A saturated aqueous NaHCO$_3$ solution (20 ml) was added to the reaction mixture and the mixture was subjected to a column of Diaion HP-20 (ca. 100 ml). The column was washed with water and eluted with aqueous CH₃CN. The yellowish fractions of the eluate were pooled and evaporated in vacuo to give a yellow amorphous solid, which was dissolved in 0.05N TsOH in MeOH (5 ml). After one hour, NaHCO₃ was added to the reaction mixture and the mixture was filtrated. The filtrate was concentrated and the residue was purified by preparative TLC to give 16 mg (13%) of the title compound.

MP 202°-205° C. IR $\nu_{max}$ (KBr) cm$^{-1}$ 1695, 1610, 1375, 1255, 1075, 780. UV $\lambda_{max}$ (MeOH)nm ($\epsilon$) 236 (34000), 266 (29500), 333 (5250), 379 (6850), 399 (10500), 421 (11300). $^1$H NMR (CDCl₃+CD₃OD) $\delta$ 1.44 (3H, s), 2.73 (3H, s), 3.48 (2H, s), 5.62 (1H, d, J=8 Hz), 5.93 (1H, d, J=4 Hz).

MS (SIMS); M/Z 738 (M+H)⁺, 404, 334, 160, 85.

What is claimed is:

1. 3',4'-O-methyoxymethylideneelsamicin A having the formula

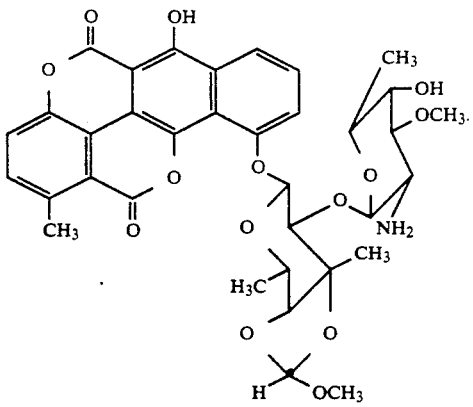

2. 4'-O-tetrahydropyranylelsamicin A having the formula:

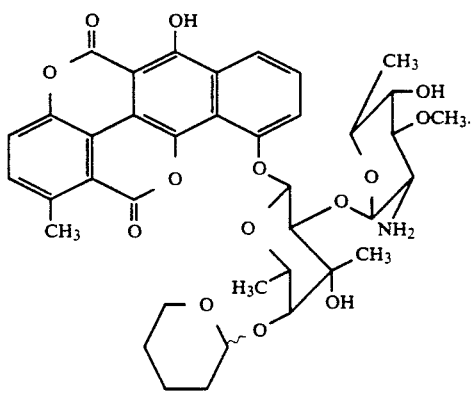

3. A pharmaceutical composition for treatment of a mammalian host affected by a tumor selected from P388 leukemia and B16 melanoma comprising an effective tumor-inhibiting amount of a compound as defined in claim 1 or 2, and a pharmaceutical carrier or diluent.

4. A method of therapeutically treating a mammalian host affected by a tumor selected rom P388 leukemia and B16 melanoma which comprises administering to said host an effective tumor-inhibiting does of a compound as defined in claim 1 or 2.

* * * * *